US010526396B2

(12) United States Patent
Lecommandoux et al.

(10) Patent No.: US 10,526,396 B2
(45) Date of Patent: Jan. 7, 2020

(54) DERIVATIVES OF ELASTIN-LIKE POLYPEPTIDES AND USES THEREOF

(71) Applicants: Centre National de la Recherche Scientifique, Paris (FR); Université de Bordeaux, Bordeaux (FR); Institut Polytechnique de Bordeaux, Talence (FR); The Regents of the University of California, Oakland, CA (US)

(72) Inventors: Sébastien Jean Marie Lecommandoux, Canejan (FR); Elisabeth Béatrice Michèle Garanger, Talence (FR); Timothy Deming, Los Angeles, CA (US)

(73) Assignees: CENTRE NATIONAL DE LA RECHERCHE SCIENTIFIQUE, Paris (FR); UNIVERSITE DE BORDEAUX, Bordeaux (FR); INSTITUT POLYTECHNIQUE DE BORDEAUX, Talence (FR); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/748,806

(22) PCT Filed: Jul. 29, 2016

(86) PCT No.: PCT/EP2016/068232
§ 371 (c)(1),
(2) Date: Jan. 30, 2018

(87) PCT Pub. No.: WO2017/021334
PCT Pub. Date: Feb. 9, 2017

(65) Prior Publication Data
US 2019/0135896 A1 May 9, 2019

(30) Foreign Application Priority Data
Jul. 31, 2015 (EP) .................................... 15306247

(51) Int. Cl.
*A61K 38/00* (2006.01)
*C07K 14/78* (2006.01)
(52) U.S. Cl.
CPC .................... *C07K 14/78* (2013.01)
(58) Field of Classification Search
None
See application file for complete search history.

(56) References Cited

U.S. PATENT DOCUMENTS

| 4,165,332 | A | 8/1979 | Beard et al. |
| 5,599,903 | A | 2/1997 | Kauvar et al. |
| 7,132,475 | B2 | 11/2006 | Hubbell et al. |
| 9,718,921 | B2 | 8/2017 | Deming et al. |

| 2010/0222407 | A1 | 9/2010 | Segura et al. |
| 2011/0177508 | A1 | 7/2011 | Bestor et al. |
| 2011/0223217 | A1 | 9/2011 | Dixon et al. |
| 2014/0294932 | A1 | 10/2014 | Kim et al. |

FOREIGN PATENT DOCUMENTS

| CN | 104926924 A | 9/2015 |
| EP | 0226827 A2 | 7/1987 |
| WO | WO-96/40757 A2 | 12/1996 |
| WO | WO-2010/023670 A2 | 3/2010 |
| WO | WO-2013/148727 A1 | 10/2013 |
| WO | WO-2016/154120 | 9/2016 |
| WO | WO-2017/021334 A1 | 2/2017 |
| WO | WO-2017/189860 | 11/2017 |

OTHER PUBLICATIONS

Alferiev et al., "High reactivity of alkyl sulfides towards epoxides under conditions of collagen fixation—a convenient approach to 2-amino-4-butyrolactones," Biomaterials, 22(18):2501-2506 (2001).
Catalog page for 2 bromoethyl triflate from ABX, http://web.archive.org/web/20090706013707/http://abx.de/chemicals/6182.html, available online Jul. 2009.
Extended European Search Report issued by the European Patent Office, dated Jan. 28, 2016, in related Application No. EP 15306247.
Gharakhanian et al., "Versatile Synthesis of Stable, Functional Polypeptides via Reaction with Epoxides," Biomacromolecules, 16(6):1802-1806 (2015).
Hanson et al., "Nonionic block copolypeptide micelles containing a hydrophobic rac-leucine core," Macromolecules, 43(15):6268-6269 (2010).
Huang et al., "Biologically active polymersomes from amphiphilic glycopeptides," J Am Chem Soc, 134:119-122 (2011).
International Search Report and Written Opinion for International Application No. PCT/EP2016/068232 dated Nov. 14, 2016.
International Search Report and Written Opinion for International Application No. PCT/US2013/033938 dated Jul. 22, 2013.
International Search Report from corresponding International Application No. PCT/US2014/018763 dated Jun. 2, 2014.
International Search Report from corresponding International Application No. PCT/US2016/023428 dated Jun. 29, 2016.
Kaplowitz et al., "The importance and regulation of hepatic glutathione," Yale J Biol Med, 54:497-502 (1981).
Kramer et al., "Glycopolypeptide conformations in bioactive block copolymer assemblies influence their nanoscale morphology," Soft Matter, 9(12):3389-95 (2013).
Kramer et al., "Preparation of Multifunctional and Multireactive Polypeptides via Methionine Alkylation," Biomacromolecules, 13:1719-1723 (2012).

(Continued)

*Primary Examiner* — Jeanette M Lieb
(74) *Attorney, Agent, or Firm* — B. Aaron Schulman, Esq.; Stites & Harbison, PLLC

(57) ABSTRACT

The present invention concerns the use of a thioether alkylation process for modulating the lower critical solution temperature of an elastin-like polypeptide comprising at least one methionine residue. It also concerns derivatives of elastin-like polypeptides and their preparation process.

16 Claims, No Drawings
Specification includes a Sequence Listing.

(56) References Cited

OTHER PUBLICATIONS

Kultyshev et al., "S-Alkylation and S-Amination of Methyl Thioethers—Derivative of closo-[B12H12]2-. Synthesis of a Boronated Phosphonate, gem-Bisposphonates, and Dodecaborane-ortho-carborane Oligomers," J Am Chem Soc, 124(11):2614-2624 (2002).
Kyte et al., "Purification of peptides that contain methionine residues," Method Enzymol, 91:367-377 (1983).
March, Jerry Advanced Organic Chemistry (1992) ISBN 0-471-60180-2, p. 294-298 and p. 352-354.
Pande et al., "Suppression of phase separation in solutions of bovine lambda IV-crestallin by polar modification of the sulfur-containing amino acids," PNAS, 88(11):4916-4920 (1991).
Reid et al., "Selective identification and quantitative analysis of methionine containing peptides by charge derivatization and tandem mass spectrometry," J Am Soc Mass Spectr, 16(7):1131-1150 (2005).
Ribeiro et al., "Influence of the amino-acid sequence on the inverse temperature transition of elastin-like polymers," Biophys J, 97:312-20 (2009).
Stark et al., "Alkylation of the methionine residues of ribonuclease in 8M urea," J Biol Chem, 269(11):3755-3761 (1964).
Storer et al., "Aracyl triflates for preparing fluorescent and UV absorbing derivatives of unreactive carboxylates, amines, and other reactive metabolites," Analytica Chimic Acta, 558:319-325 (2006).
Supplementary European Search Report dated Sep. 16, 2016 from EP 14 75 7627.
Taichi et al., "Suppression of side reactions during final deprotection employing a strong acid in boc chemistry: regeneration of methionyl residues from their sulfonium salts," Int J Peptide Res Ther, 15(4):247-253 (2009).
Teeuwen et al., "'Clickable' elastins: elastin-like polypeptides functionalized with azide or alkyne groups," Chem Comm, 27:4022-4024 (2009).
Toennies et al., "Methionine Studies VII. Sulfonium Derivatives," J Am Chem Soc, 67(5):849-851 (1945).
Umemura et al., "Alylation of several nucleophiles with alkylsulfonium salts," Bull Chem Soc Japan, 63(9):2593-2600 (1990).
Gharakhanian et al., "Chemoselective synthesis of functional homocysteine residues in polypeptides and peptides," Chem Commun, 52(30): 5336-5339 (2016).
Gharakhanian et al., "Role of side-chain molecular features in tuning lower critical solution temperatures (LCSTs) of oligoethylene glycol modified polypeptides," J Phys Chem B, 120(26): 6096-6101 (2016).
International Search Report and Written Opinion for International Application No. PCT/US2017/029867 dated Jul. 20, 2017.
Notice of Allowance and Fees Due for U.S. Appl. No. 15/559,981 dated Feb. 25, 2019.
U.S. Appl. No. 14/388,777, Abandoned.
U.S. Appl. No. 14/770,417, Granted.
U.S. Appl. No. 15/559,981, Pending.
U.S. Appl. No. 15/559,981, Allowed.
U.S. Appl. No. 16/096,951, Pending.

DERIVATIVES OF ELASTIN-LIKE POLYPEPTIDES AND USES THEREOF

RELATED APPLICATIONS

This application is the U.S. National Stage of International Patent Application No. PCT/EP2016/068232, filed Jul. 29, 2016, which claims priority to European Application No. 15306247.6, filed Jul. 31, 2015, the contents of each of which are expressly incorporated herein by reference in their entireties.

SEQUENCE LISTING

The present disclosure contains a Sequence Listing that has been submitted electronically in ASCII format, which is hereby incorporated by reference in its entirety. Said ASCII copy, created on Jun. 29, 2018, is named UCH-09101 (32246.09101)_SL.txt and is 7,824 bytes in size.

The present invention concerns derivatives of elastin-like polypeptides, as well as a process for their preparation. It also concerns uses of such derivatives.

While commonly exploited in biology basic research, as well as in biotech and pharmaceutical industries to produce recombinant proteins and therapeutics, protein engineering techniques are rapidly advancing the field of polymer science, paving the way to precision protein-like polymers with exquisite control over primary structure, namely monomer sequence, and molecular weight. In addition to silk-based proteins that have been developed mainly for tissue engineering and drug-delivery, recombinant elastin-like polypeptides (ELPs) are emerging as a unique class of precision polymers with stimuli-responsive self-assembly properties for specific biomedical and biotechnological applications.

ELPs are repeating sequences of [-Val-Pro-Gly-Xaa-Gly-] pentapeptide (SEQ ID NO: 3), the guest residue Xaa being any amino acid except proline, originally inspired from the hydrophobic domain of tropoelastin. ELPs exhibit a lower critical solution temperature (LCST), also referred as an inverse temperature transition (Tt), similar to synthetic polymers such as poly(N-isopropylacrylamide) (pNIPAM). ELP chains are fully soluble in water below the LCST, while switching to an insoluble state above the LCST. Fully reversible, the aggregation is influenced by different parameters such as the nature of the Xaa guest residues within the ELP repeats, the overall molecular weight and molar concentration of the ELP, and the ionic strength of the solution (Meyer, D. E.; Chilkoti, A. Biomacromolecules 2004, 5, 846-851; McDaniel, J. R.; Radford, D. C.; Chilkoti, A. Biomacromolecules 2013, 14(8), 2866-2872). This solubility switch has proven to be a major advantage for the purification of recombinant ELPs from bacterial lysates, as well as for the controlled self-assembly of individual ELP blocks.

Post-polymerization modifications of ELPs reported so far have mostly involved their chain ends. Different ELP sequences have been conjugated to small organic molecules, oligonucleotides, drugs, or poly(ethylene glycol) PEG. Modifications at the amino acid side chains within the ELP domain have been more scarcely reported. Such modifications require the use of highly efficient reactions in order to successfully modify all the repeating functional groups in these sequences in high yield. These modifications also require the use of bioorthogonal ligation strategies to chemoselectively modify residue-specific side chains without affecting the amino acid backbone, C- and N-terminal ends and side chain groups of other residues.

The aim of the present invention is to provide modified recombinant elastin-like polypeptides, using chemical modifications.

Another aim of the present invention is to provide a chemoselective process for preparing modified elastin-like polypeptides on the Xaa guest residue.

Another aim of the present invention is to provide derivatives of elastin-like polypeptides, the lower critical solution temperature of which being modified in comparison with the starting elastin-like polypeptides.

Another aim of the present invention is to provide an easy method for modulating the lower critical solution temperature of elastin-like polypeptides, without any support from biotechnology.

The present invention relates to a compound comprising at least one repetitive unit having the following formula (I):

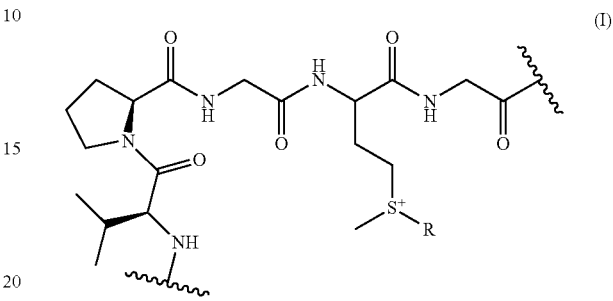

wherein R is selected from the group consisting of:
$(C_1-C_{22})$alkyl groups;
said alkyl groups being possibly substituted by one or several substituents selected from the group consisting of: OH, $OR_a$, $NR_bR_c$, and $NHC(O)R_c$,
  $R_a$ being selected from the group consisting of: $(C_1-C_{10})$alkyl groups possibly interrupted by one or several heteroatom(s)(such as O, NH or S), $(C_1-C_{10})$alkylene-$(C_2-C_{10})$alkyne groups, $(C_1-C_{10})$alkylene-$(C_2-C_{10})$alkenyl groups, and $(C_1-C_{10})$alkylene-X' groups;
X' representing a radical having the following formula:

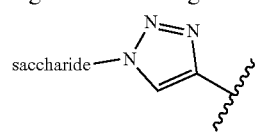

$R_b$ and $R_c$ representing independently from each other H or a $(C_1-C_{10})$alkyl group;
$(C_1-C_{22})$alkylene-$(C_6-C_{30})$aryl groups;
$(C_6-C_{30})$aryl groups;
$(C_2-C_{22})$alkyne groups; and
saccharides.

The compounds of formula (I) are derivatives of elastin-like polypeptides (ELP). They correspond to modified ELP wherein at least one methionine residue is thioalkylated. In other words, the compounds of formula (I) are modified ELP wherein the sulfur atom of the methionine residue is alkylated (presence of the R group as defined above).

The present invention also relates to a compound comprising at least one repetitive unit having the following formula (I'):

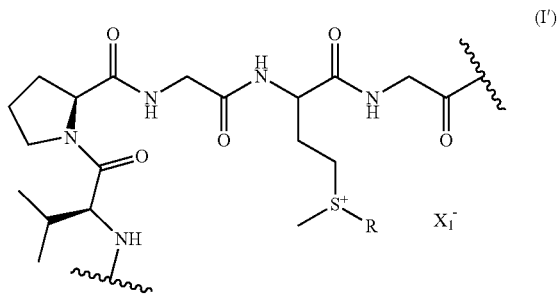

wherein:

R is as defined above in formula (I), and $X_1$ is a counterion, preferably chosen from anionic monovalent counterions.

Preferably, $X_1$ is chosen from: $Cl^-$, $Br^-$, $I^-$, $CH_3COO^-$, $CF_3COO^-$, $PF_6^-$, $NTf_2^-$,

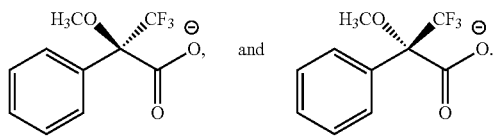

According to the present invention, the expression "$C_1$-$C_z$" means a carbon-based chain which can have from t to z carbon atoms, for example $C_1$-$C_3$ means a carbon-based chain which can have from 1 to 3 carbon atoms.

According to the present invention, the term "a halogen atom" means a fluorine, a chlorine, a bromine or an iodine.

According to the present invention, the term "an alkyl group" means a linear or branched, saturated or unsaturated, hydrocarbon-based aliphatic group comprising, unless otherwise mentioned, from 1 to 22, preferably from 1 to 10 carbon atoms. By way of examples, mention may be made of methyl, ethyl, n-propyl, isopropyl, butyl, isobutyl, tert-butyl or pentyl groups. According to a preferred embodiment, the alkyl groups comprise from 1 to 6 carbon atoms, in particular from 1 to 4 carbon atoms.

According to the invention, the alkyl group may also comprise one or several insaturations.

According to the present invention, the term "aryl group" means a cyclic aromatic group comprising between 6 and 30 carbon atoms, and preferably between 6 and 10 carbon atoms. By way of examples of aryl groups, mention may be made of phenyl or naphthyl groups.

When an alkyl radical is substituted with an aryl group, the term "arylalkyl" or "aralkyl" radical is used. The "arylalkyl" or "aralkyl" radicals are aryl-alkyl-radicals, the aryl and alkyl groups being as defined above. Among the arylalkyl radicals, mention may in particular be made of the benzyl or phenethyl radicals.

The abovementioned "alkyl", "alkylene" and "aryl" radicals can be substituted with one or more substituents. Among these substituents, mention may be made of the following groups: amino, hydroxyl, thiol, oxo, halogen, alkyl, alkoxy, alkylthio, alkylamino, aryloxy, arylalkoxy, cyano, trifluoromethyl, carboxy or carboxyalkyl. Preferably, the alkyl substituents are chosen from the group consisting of: amino, hydroxyl, alkoxy, and alkylamino, and most preferably are hydroxyl or alkoxy.

As used herein, the term "alkylene" (or "alkylidene") refers to a divalent radical comprising from 1 to 22, preferably from 1 to 10 carbon atoms, and preferably from 1 to 6 carbon atoms, and more preferably 1 to 4 carbon atoms. When said radical is linear, it may be represented by the formula $(CH_2)_k$ wherein k is an integer varying from 1 to 22, and preferably from 1 to 6. The following alkylene radicals may be cited as example: methylene, ethylene, propylene, butylene, pentylene, or hexylene.

According to the present invention, the term "alkyne group" means a hydrocarbon group comprising at least one triple bond. Preferably, it refers to a —C≡CH group.

According to the present invention, the term "alkenyl group" means a hydrocarbon group comprising at least one double bond. Preferably, it refers to a —CH=$CH_2$ group.

According to the invention, the expression "($C_1$-$C_{22}$) alkylene($C_2$-$C_{22}$)alkyne group" refers to an alkylene radical substituted by an alkyne group.

According to the invention, the expression "($C_1$-$C_{22}$) alkylene-($C_6$-$C_{10}$)aryl group" refers to an alkylene radical substituted by an aryl group, in particular an alkylene radical substituted by a phenyl group.

According to the present invention, the term "saccharides" refers to mono-, di-, oligo- or polysaccharides.

The present invention also relates to compounds having the following formula (II):

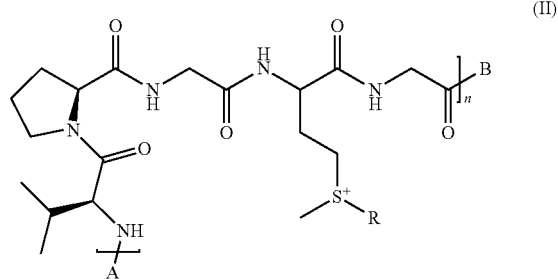

wherein:

n is an integer varying from 1 to 200, and

R is as defined above in formula (I); and

A is selected from the group consisting of: H, acetyl, natural or unnatural amino acids, peptides, proteins or synthetic polymers; and B is selected from the group consisting of: OH, $NH_2$, NHAc, natural or unnatural amino acids, peptides, proteins, or synthetic polymers.

The present invention also relates to a compound comprising at least one repetitive unit having the following formula (II'):

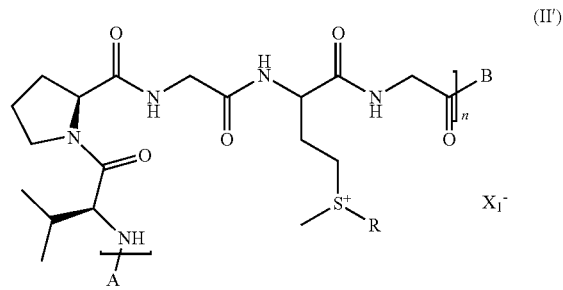

wherein:

A, B, n, and R are as defined above in formula (II), and $X_1$ is a counterion, preferably chosen from anionic monovalent counterions.

According to the invention, the term "amino acids" refers to both natural and synthetic amino acids.

As used herein, the term "amino acid" is understood to include: the 20 naturally occurring amino acids i.e. alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine; amino acids harbouring the post-translational modifications which can be found in vivo such as hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

In the context of the invention, the terms "polypeptide" and "peptide" are used indifferently and refer to native peptides (either proteolysis products or synthetically synthesized peptides) and further to peptidomimetics, such as peptoids and semipeptoids which are peptide analogs, which may have, for example, modifications rendering the peptides more stable while in a body, or more or less immunogenic. Such modifications include, but are not limited to, cyclization, N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptidomimetic compounds are well known in the art and are specified in Quantitative Drug Design, CA. Ramsden Gd., Chapter 17.2, F. Choplin Pergamon Press (1992).

According to the invention, a peptide consists of less than 50 amino acids, preferably less than 40 amino acids, more preferably less than 30 amino acids, still preferably less than 20 amino acids.

According to the invention, the term "synthetic polymers" refers to any polymer obtained by a polymerization method involving reactive monomer(s), such as anionic, cationic, radical or ring opening polymerization. The most common polymers are: polyacrylates, polymethacrylates, polystyrenics, polyethers, polyesters, polycarbonates and polyamides.

According to a preferred embodiment, A is selected from the group consisting of peptides and natural or unnatural amino acids.

According to an embodiment, A represents a succession of several amino acids, which may in particular include one or several repeating sequences -Val-Pro-Gly-Xaa-Gly-, Xaa being any amino acid except proline (SEQ ID NO: 3).

A may in particular include one or several repeating sequences -Val-Pro-Gly-Val-Gly- (SEQ ID NO: 4).

According to a preferred embodiment, B is OH, $NH_2$, NHAc (Ac representing an acetyl group) or is selected from the group consisting of peptides and natural or unnatural amino acids. Most preferably, B is OH, or is selected from the group consisting of peptides and natural or unnatural amino acids.

According to an embodiment, B represents a succession of several amino acid residues, which may in particular include one or several repeating sequences -Val-Pro-Gly-Xaa-Gly-, Xaa being any amino acid except proline (SEQ ID NO: 3).

B may in particular include one or several repeating sequences -Val-Pro-Gly-Val-Gly- (SEQ ID NO: 4).

A preferred compound according to the invention has the following formula (III):

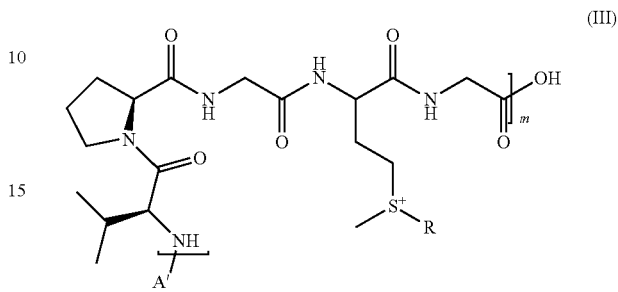

(III)

wherein:
m is an integer varying from 1 to 200, preferably from 20 to 200, and
R is as defined above in formula (I); and
A' is a peptide comprising from 1 to 20 amino acids.

The present invention also relates to a compound comprising at least one repetitive unit having the following formula (III'):

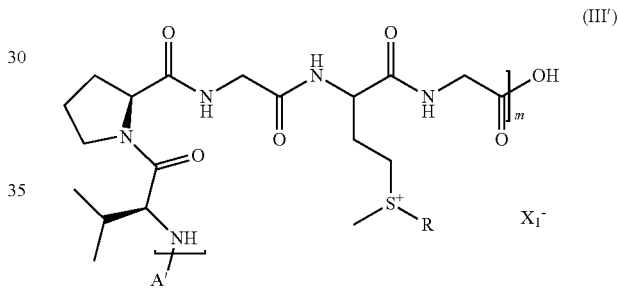

(III')

wherein:
A', m, and R are as defined above in formula (III), and
$X_1$ is a counterion, preferably chosen from anionic monovalent counterions.

Another preferred compound according to the invention has the following formula (IV):

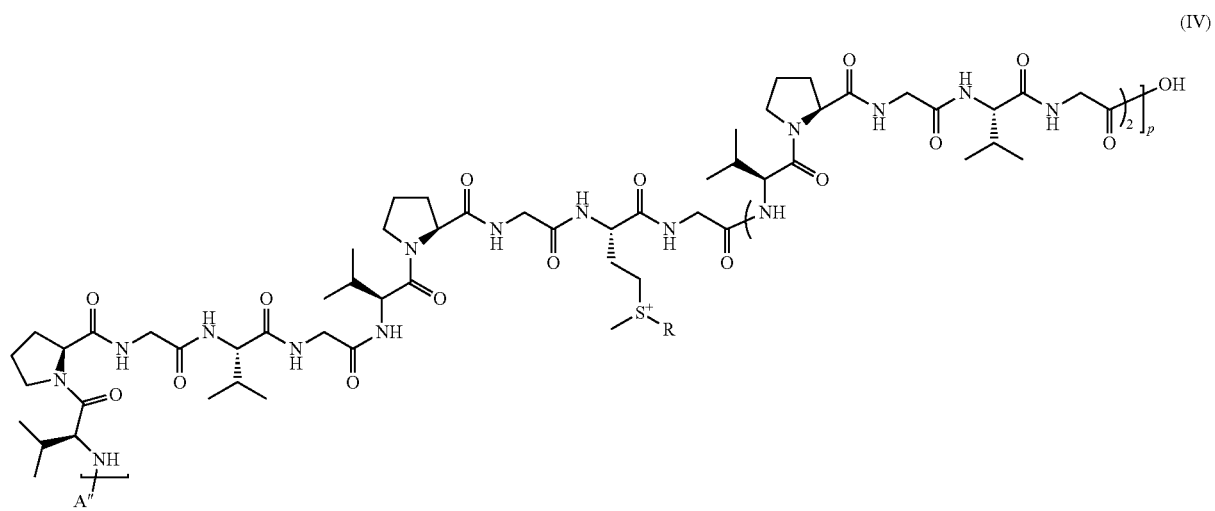

(IV)

wherein:
p is an integer varying from 1 to 200, preferably from 5 to 200, and
R is as defined above in formula (I); and
A" is a peptide comprising from 1 to 20, preferably from 1 to 8, amino acids.

The present invention also relates to a compound comprising at least one repetitive unit having the following formula (IV'):

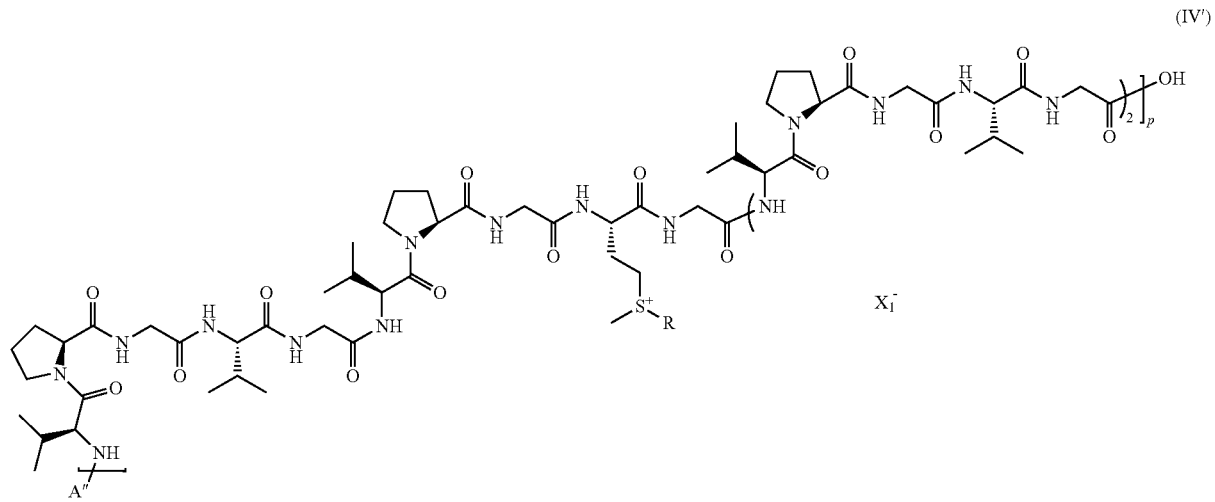

(IV')

wherein:
A", p, and R are as defined above in formula (IV), and
$X_1$ is a counterion, preferably chosen from anionic monovalent counterions.

According to an embodiment, in formula (I), (I'), (II), (II'), (III), (III'), (IV) or (IV'), R is selected from the group consisting of:
($C_1$-$C_{22}$)alkyl groups; and
($C_0$-$C_{22}$)alkylene-phenyl groups.

Preferably, R is a ($C_0$-$C_4$)alkyl or benzyl group, and more preferably R is —$CH_3$, —($CH_2$)$_3$—$CH_3$, or —$CH_2$—$C_6H_5$.

According to an embodiment, in formula (I), (I'), (II), (II'), (III), (III'), (IV) or (IV'), R is a group -$A_1$-CH(OH)-$A_2$-O-$A_3$-$A_4$, wherein:
$A_1$ is a ($C_1$-$C_4$)alkylene radical;
$A_2$ is a ($C_1$-$C_4$)alkylene radical;
$A_3$ is a ($C_1$-$C_4$)alkylene radical or a —($CH_2$—$CH_2$—O)$_i$— group, i being an integer varying from 1 to 4, and
$A_4$ is a ($C_1$-$C_4$)alkylene radical or a ($C_2$-$C_4$)alkyne group.

When $A_3$ is a —($CH_2$—$CH_2$—O)$_i$— group, the bond between $A_3$ and $A_4$ corresponds to a bond between the oxygen atom of the last repeating unit —$CH_2$—$CH_2$—O— and the first carbon atom of $A_4$.

According to an embodiment, $A_1$ and $A_2$ are —$CH_2$—.

According to an embodiment, $A_3$ is a ($C_1$-$C_4$)alkylene radical and $A_4$ is a ($C_2$-$C_4$)alkyne group. More preferably, $A_3$ is —$CH_2$— and $A_4$ is a ethynyl radical —C≡CH.

According to an embodiment, $A_3$ is a —($CH_2$—$CH_2$—O)$_i$— group, and $A_4$ is a ($C_1$-$C_4$)alkylene radical. Preferably, $A_3$ is a —($CH_2$—$CH_2$—O)$_2$— group or a —($CH_2$—$CH_2$—O)$_3$— group. Preferably, $A_3$ is —$CH_3$ or —$CH_2$—$CH_3$.

The preferred R groups according to the invention are:

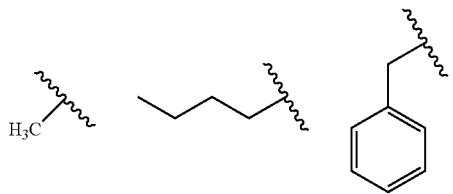

-continued

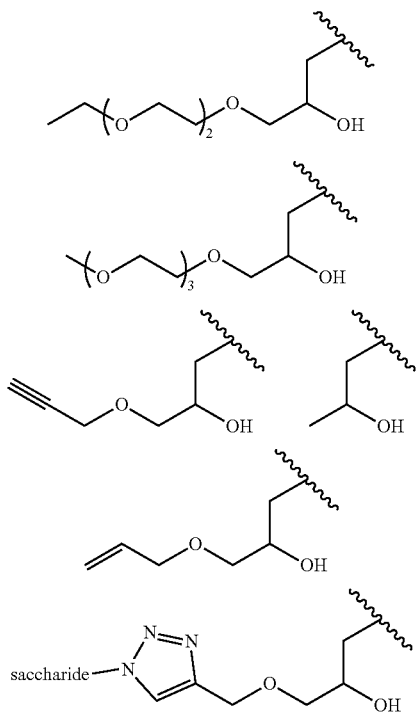

wherein the symbol ⸺ indicates the bond with the sulfur atom in formula (I).

The present invention also relates to a thioether alkylation process for preparing a compound according to the invention comprising a thioether alkylation step of an elastin-like polypeptide comprising at least one repetitive unit having the following formula (V):

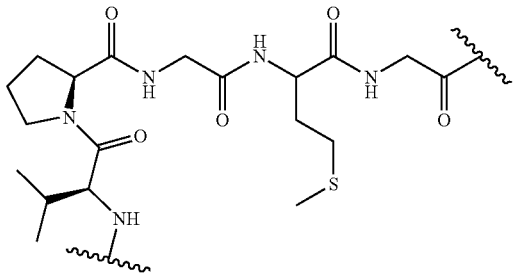

said thioether alkylation step consisting in the reaction with an alkylation agent.

According to an embodiment, said thioether alkylation step consists in the reaction with a compound of formula (III) R—X, R being as defined above, and X being a halogen atom.

According to an embodiment, said thioether alkylation step consists in the reaction with a compound of formula (III-1):

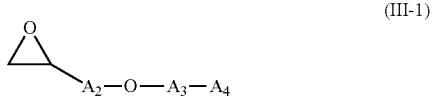

$A_2$, $A_3$, and $A_4$ being as defined above.

Such embodiment corresponds to the preparation of compounds of the invention wherein R is -$A_1$-CH(OH)-$A_2$-O-$A_3$-$A_4$.

Preferably, the alkylation agent is a compound of formula (III) or a compound of formula (III-1).

According to an embodiment, the above-mentioned alkylation step is carried out in at least one solvent.

The preferred solvents according to the invention are chosen from the group consisting of: methylene chloride, formic acid, DMSO, and hexafluoroisopropanol (HFIP).

Preferably, the above-mentioned alkylation step is carried out at a temperature comprised between 20° C. and 50° C.

According to an embodiment, the compounds of formula (I) are prepared at ambient temperature.

Therefore, the present invention relates to the use of a thioether alkylation process for modifying an elastin-like polypeptide comprising at least one methionine residue at the Xaa position.

The present invention also relates to the use of a thioether alkylation process for modulating the lower critical solution temperature of an elastin-like polypeptide comprising at least one methionine residue.

Preferably, the ELP used according to the invention comprises at least one repetitive unit having the formula (V) as defined above.

The present invention also relates to a process for modulating the lower critical solution temperature of a an elastin-like polypeptide, said process comprising the thioether alkylation step of an elastin-like polypeptide comprising at least one repetitive unit having the formula (V) as defined above.

According to the invention, the term "lower critical solution temperature" (LCST) or "inverse temperature transition" ($T_t$) refers to the temperature which results in the transition of ELP from a soluble to an insoluble form. ELP are fully soluble in water below the LCST, while switching to an insoluble state above the LCST. Especially, by heating an aqueous solution of the ELP, this ELP becomes insoluble in water.

According to the invention, the term "modulating" includes the terms "increasing" and "reducing".

Indeed, surprisingly, the use of the thioether alkylation process allows modifying the LCST of the ELP.

To this date, in order to modify the LCST of ELP, the polypeptide chain of the ELP was modified by a biotechnology method, which was a very complex and long process, requesting molecular biology and bioproduction optimization steps. In other words, no chemical process involving the Xaa residue has been used for modulating the LCST yet. However, the modulation process of the invention is a chemical process very easy to be implemented and which is also precise and selective.

According to an embodiment of the process for modulating the lower critical solution temperature, the thioether alkylation step consists in reacting the elastin-like polypeptide with an alkylation agent.

According to an embodiment, the thioether alkylation step consists in reacting the elastin-like polypeptide with a compound of formula (III) R—X, R being as defined above in formula (I), and X being a halogen atom.

According to an embodiment of the process for modulating the lower critical solution temperature, the thioether alkylation step consists in reacting the elastin-like polypeptide with a compound of formula (III-1) as defined above.

The present invention also relates to the use of the modified ELP according to the invention, such as those of formula (II), as drug carrier.

The present invention also relates to the use of the modified ELP according to the invention, such as those of formula (II), for the preparation of a conjugate between said compound and a drug.

The present invention also relates to the use of the modified ELP according to the invention, such as those of formula (II), for protein purification.

The present invention also relates to the use of the modified ELP according to the invention, such as those of formula (II), for removal of heavy metals from a contaminated medium.

EXAMPLES

Materials and Methods

Materials.

LB medium, bacto-tryptone, and yeast extract were purchased from BD Biosciences (Le Pont-de-Claix, FR). Ampicillin was obtained from Eurobio (Courtaboeuf, FR). Glucose and polyethyleneimine (PEI) were purchased from Sigma-Aldrich (Lyon, FR). Isopropyl 1-D-thiogalactopyranoside (IPTG) was obtained from QBiogene (Illkirch, FR). Complete mini EDTA-free protease inhibitors were purchased from Roche Diagnostics (Mannheim, DEU). Deionized water (18 MΩ-cm) was obtained by passing in-house deionized water through a Millipore Milli-Q Biocel A10 purification unit. THF was purchased from Thermo Fisher Scientific (Waltham, Mass. USA). Methyl iodide, benzyl bromide, and formic acid were purchased from Sigma Aldrich (St. Louis, Mo., USA).

Example 1: Preparation of ELP20

ELP20 is an ELP comprising 20 repeating units of formula (V) as defined above.

A 13 amino acid-long sequence termed Leader was introduced at the N-terminal end of the ELP domain to provide an initial methionine for proper initiation of translation in *E. coli*, a tryptophan for detection purposes and additional residues for optimal production of ELP20 in the bacterial host.

SEQ ID NO: 1 corresponds to the oligonucleotide sequence and SEQ ID NO: 2 corresponds to the protein sequence of ELP20 synthetic gene and polypeptide.

Bioproduction of Recombinant ELP20.

A single bacterial colony was selected and cultured overnight at 37° C. on a rotary shaker at 200 rpm in 50 mL rich LB medium (1% bacto-tryptone, 0.5% NaCl, 1% yeast extract) containing 100 µg·mL$^{-1}$ ampicillin. The seed culture was inoculated into 0.95 L rich LB medium supplemented with glucose (1 g·L$^{-1}$) and ampicillin (100 µg·mL$^{-1}$), and bacteria were cultivated at 37° C. in a multi-bioreactor system with three independent 1 L-vessels process control (BIOSTAT® Qplus, Sartorius Stedim Biotech, Germany). The pH was maintained at 7 with 1 M phosphoric acid and 1 M sodium hydroxide. The dissolved oxygen tension pO$_2$ was kept above 15% by adjusting agitation rate (150-600 rpm) and air flow (1-1.5 L·min$^{-1}$). When the optical density at 600 nm (OD$_{600}$) reached the value of 1.2, IPTG was added to a final concentration of 0.5 mM and the temperature of cultivation was decreased to 25° C. Samples were then collected every hour for measurement of OD$_{600}$.

Isolation and Purification of Recombinant ELP20.

After 5 hrs IPTG-induction, the culture was harvested by centrifugation at 7,500 g and 4° C. for 15 min. The cell pellet was resuspended with 10 mL·g$^{-1}$ (wet weight) phosphate buffer (PBS; NaCl 137 mM, KCl 2.7 mM, Na$_2$HPO$_4$ 8 mM, KH$_2$PO$_4$ 2 mM, pH 7.4) supplemented with one tablet/10 mL of Complete mini EDTA-free protease inhibitors. The mixture was incubated overnight at −80° C. and slowly defrosted by incubation at 4° C. Cell lysis was completed by sonication at 15° C. with sequential 4 sec-pulses at 125 W separated by 9 sec-resting time periods for a total duration of 15 min. PEI was then added at a final concentration of 0.44% (v/v) to precipitate bacterial DNA. Insoluble debris was removed by centrifugation at 16,000 g and 4° C. for 30 min. The cleared lysate was thereafter subjected to three successive rounds of Inverse Transition Cycling (ITC). Briefly, ELP20 polypeptide was precipitated with NaCl at 25° C. and retrieved by centrifugation at 16,000 g and 25° C. for 30 min ("warm spin"). After removal of soluble proteins in the supernatant, ELP20-containing pellet was resuspended in cold PBS. Insoluble, heat denatured proteins from *E. coli* were eliminated in the pellet after centrifugation at 16,000 g and 4° C. for 15 min ("cold spin"), while the ELP20-containing supernatant was subjected to an additional ITC. Final concentrations of NaCl used before each "warm spin" were 1.5, 0.7 and 0.5 M for the first, second and third ITC rounds, respectively. Soluble ELP20 was then extensively dialyzed against ultrapure water at 4° C. using 1 kDa MWCO-dialysis tubing (Spectra Por7) and lyophilized. The purity and average MW of ELP20 were assessed by SDS-PAGE using 15% TRIS-glycine gels stained with colloidal blue G250.

Mass Spectrometry Analysis of ELP20.

Mass spectrometry analysis was performed on a ESI-Q-TOF (Q-TOF Premier, Waters, Manchester, UK). All solvent used were HPLC grade. Lyophilized ELP20 was resuspended in DMSO and then diluted in H$_2$O/MeOH (1:1 v/v). The solution was diluted in methanol/0.1% aqueous formic acid (1:1 v/v) to a final concentration of around 10 µmol·µL$^{-1}$ and infused into the electrospray ionization source at a flow rate of 10 µL·min$^{-1}$. The mass spectrometer was operated in the positive mode with external calibration performed with a solution of the standard protein Apomyoglobin at a concentration of 1 µmol·µL$^{-1}$ in acetonitrile/0.1% aqueous formic acid (1:1 v/v). ELP20 spectrum was deconvoluted by the Waters software MaxEnt using a maximum entropy-based approach. Theoretical average molecular mass of ELP20 is 10,381.64 Da. Experimental [M+H]$^+$=10,382.0.

NMR Spectrometry Analysis of ELP20.

Phase-sensitive HSQC experiment was used to acquire the 2D spectra giving DEPT-type information in addition to the $^1$H-$^{13}$C connectivity. This experiment was performed at 298 K on a Bruker Avance III HD NMR spectrometer operating at 400.3 MHz (100.7 MHz for the carbon). The $^1$JCH used was 145 Hz. 128 scans were used with a recycle delay of 2 sec. COSY experiment was performed at 298 K on the same spectrometer. 256 scans were recorded with a recycle delay of 2 sec. The DMSO signal was used as the reference signal (δ=2.50 ppm). Data processing was performed using Topspin software. Chemical shifts of amino acids are well known in the literature. With Phase-sensitive HSQC, CH$_n$ spin vectors develop differently after a 90° pulse depending on how many hydrogens are bonded to the carbon atom. CH and CH$_3$ vectors have opposite phase compared with CH$_2$. We have identified the CH$_3$ of valine at 0.85-0.90 ppm (18.9-19.5 ppm for $^{13}$C) and used it as reference for the calibration of integrations. After examination of COSY spectra, we determined the resonances for each amino acid. Assignments of ELP20 were done with the help of COSY and HSQC.

Example 2: Methionine Alkylation of ELP20

ELP20 samples were reacted with alkylating reagents with the aim of both evaluating the efficacy of this bioconjugation reaction on these protein substrates, and for measuring the resulting effect on the chain properties (LCST and conformation).

General Procedure

ELP20 was dissolved in 0.2 M aqueous formic acid (20 mg·mL$^{-1}$). Alkyl halide (15 equiv. per Met residue) was added as a solution in THF (50 mg·mL$^{-1}$). The reaction was sealed, covered with foil, and stirred for 5 days at room temperature. Diethyl ether (equal to about half the reaction volume) was then added to the reaction to extract the excess alkyl halide. The biphasic reaction was vortexed briefly and allowed to sit to allow separation of the organic and aqueous phases. The ether layer was pipetted off and discarded. The reaction mixture was then transferred to 2,000 MWCO dialysis tubing and dialyzed against 0.1 M NaCl for 24 hours to exchange all counterions to chloride, followed by dialysis against ultrapure water for 48 hours with frequent water changes. The product was lyophilized to dryness to give a white powder in ~85% yield.

Chemoselective Methionine Alkylation Reaction of ELP20.

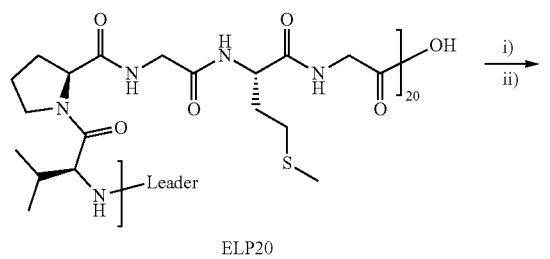

ELP20

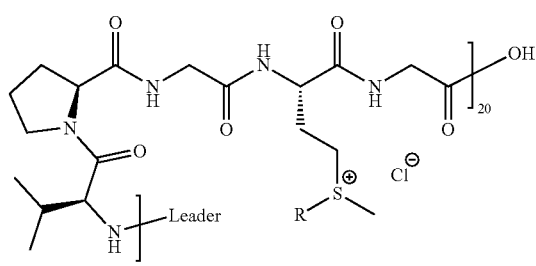

ELP20(Me): R = CH$_3$
ELP20(Bn): R = CH$_2$—C$_6$H$_5$ i) 0.2M HCOOH, R—X (CH$_3$I or BnBr) in THF, rt, 5 days
ii) Dialysis (0.1M NaCl and H$_2$O)

Methionine residues of ELP20 were first methylated using methyl iodide to measure the effect of the conversion from a thioether group to a positively-charged sulfonium on the LCST. Quantitative methylation was obtained with 15 equivalents of MeI per methionine, and the reactions were performed under acidic conditions (0.2 M formic acid in water) to favor reaction at methionine. Excess methyl iodide was easily removed after reaction by liquid-liquid extraction with diethyl ether. While alkylations of methionine residues in synthetic polypeptides proceed rapidly with near stoichiometric amounts of alkylating reagent, it was found that ELP20 was slower to react, and excess alkylating agents were used to ensure complete modification of all methionine residues.

Syntheses and Characterizations of ELP20(Me) and ELP20(Bn).

ELP20(Me) and ELP20(Bn) were prepared from 10.3 mg ELP20 and either methyl iodide or benzyl bromide, respectively, using the general procedure described above.

ELP20(Me) and ELP20(Bn) were characterized by $^1$H NMR. $^1$H NMR spectra were recorded on Bruker spectrometers at 500 MHz at ambient temperature, and are calibrated relative to the D$_2$O solvent signal at 4.78 ppm. Integrations were calibrated to the 6 valine methyl protons at 0.9 ppm.

Similar to above, a bulkier benzyl group was introduced at each methionine side chain of ELP20 using 15 equivalents of benzyl bromide. ELP20(Bn) was separated from the excess BnBr after extraction with Et$_2$O, followed by dialysis and lyophilization. The degree of benzylation was again assessed using $^1$H NMR analysis. Calibrating our integrations to valine methyl groups as above, we observed the appearance of resonances at δ=7.47 and 7.54 ppm that integrated for 5 protons and were assigned to the phenyl group of the sulfonium. The resonance at δ=4.66 ppm that integrated for two protons was assigned to the methylene of the benzyl group. The resonance of the methionine methyl group was shifted from δ=2.09 ppm in the ELP20 spectrum to δ=2.81 ppm in ELP20(Bn).

Synthesis and Characterization of ELP20(Bu)

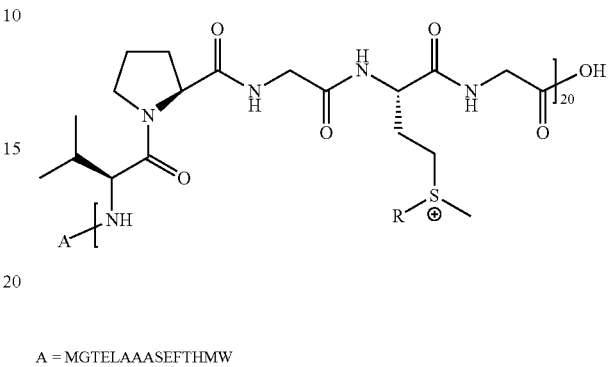

A = MGTELAAASEFTHMW
R being ——(CH$_2$)$_3$—CH$_3$ (Bu).

Synthesis of Butyl Triflate (CH$_3$—(CH$_2$)$_3$-OTf; BuOTf):

Pyridine (1.06 equiv.) was added to anhydrous dichloromethane (DCM, 15 mL) under inert atmosphere (N$_2$) and the solution was cooled for a couple of minutes using a methanol/liquid nitrogen bath (−20° C.). Triflic anhydride (1.01 equiv.) was added dropwise and the mixture was stirred for 5 minutes. Butanol (1 equiv.) was added dropwise. After addition, the reaction mixture was stirred for few minutes at −20° C., then removed from the cold bath, and allowed to return slowly to room temperature. The reaction mixture was diluted with an equal volume of hexane and pushed through a 50 mL silica plug with a DCM/hexane solvent system (50:50). Fractions of product were collected and evaporated under reduced pressure at room temperature to provide a colorless liquid.

Synthesis of ELP20(Bu):

A-[VPGMG]$_{20}$ (SEQ ID NO: 2) was suspended in anhydrous DCM (10 mg·mL$^{-1}$) resulting in a whitish dispersion. BuOTf (15 equiv. per methionine residue) was added and the reaction mixture was stirred at room temperature under inert atmosphere (N$_2$) for 48 hours. The reaction mixture was precipitated in ether to remove excess butyl triflate and evaporated under vacuum at room temperature to give the product as a white solid. The powder was dispersed in a mixture of water and acetonitrile (1:1), transferred into 2,000 MWCO dialysis tubing and dialyzed against 0.1 M NaCl for 24 hours and deionized water for 48 hours with frequent water changes. The solution was then lyophilized to provide ELP20(Bu) as a white solid. ELP20(Bu) was identified by $^1$H NMR (300 MHz, D$_2$O, 25° C.) (main peaks, one (VPGMG (SEQ ID NO: 6)) repeat unit): δ 3.45-3.29 (br m, 4H, SCH$_2$), 2.92 (br s, 3H, SCH$_3$), 1.87-1.77 (br m, 2H, CH$_2$ Bu chain), 1.54-1.47 (br m, 2H, CH$_2$ Bu chain), 1.04-0.92 (br m, 9H, CH$_3$ Val+CH$_3$ Bu chain).

Example 3: Preparation of Other Alkylated ELP

The following modified ELPs (compounds 4 to 8) have been prepared and characterized:

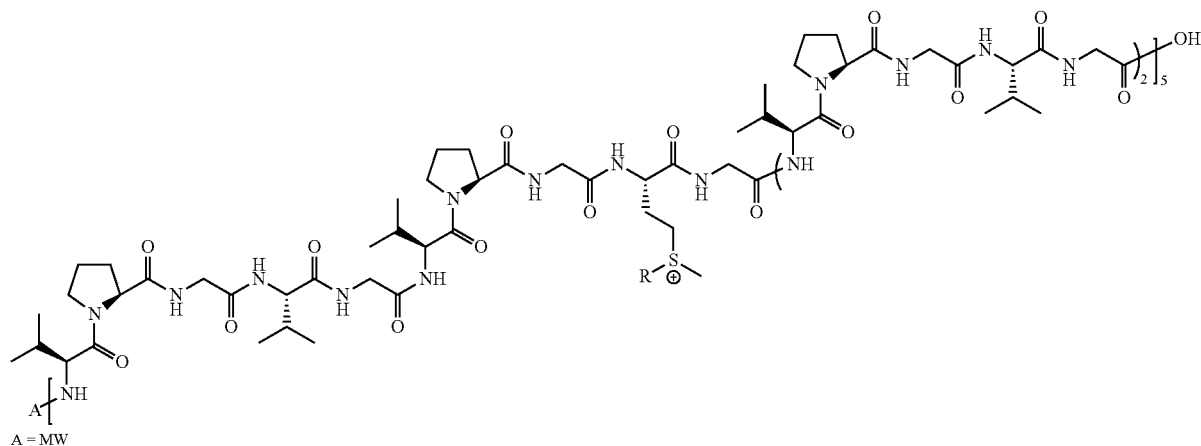
A = MW
| Cpd # | Chemical structure of R group at each methionine side chain | MW (g. mol⁻¹) |
|---|---|---|
| 4 | ethyl-(OCH₂CH₂)₂-O-CH₂-CH(OH)-CH₂- | 9,363 |
| 5 | H-(OCH₂CH₂)₃-O-CH₂-CH(OH)-CH₂- | 9,483 |
| 6 | HC≡C-CH₂-O-CH₂-CH(OH)-CH₂- | 9,567 |
| 7 | H-(OCH₂CH₂)₃-O-CH₂-CH(OH)-CH₂- | 18,278 |
| 8 | HC≡C-CH₂-O-CH₂-CH(OH)-CH₂- | 18,498 |
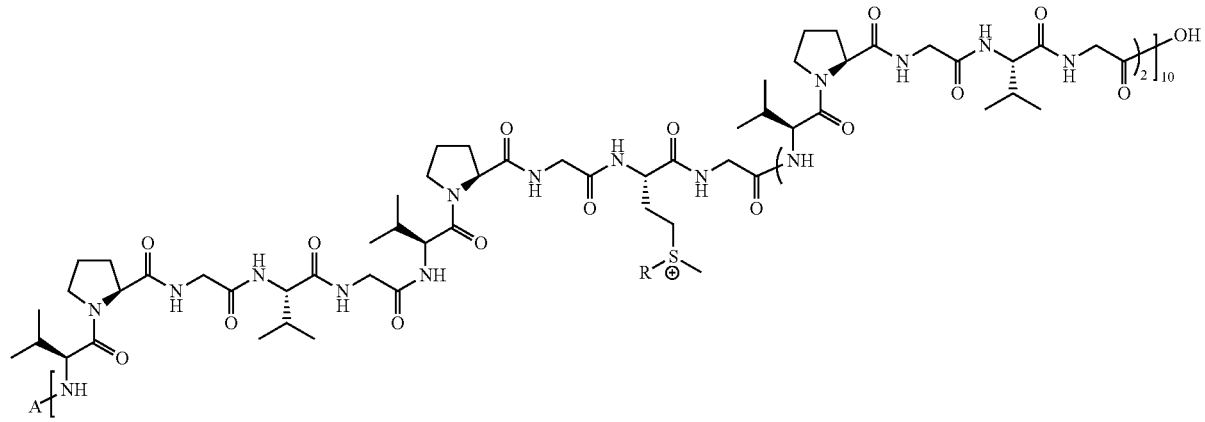
A = MW Experimental Procedures Synthesis of Epoxide a:

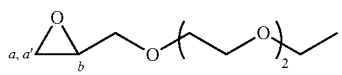

Diethylene glycol monoethyl ether (1 equiv.) and water (1 mL) were mixed together and stirred on ice before addition of NaOH (2.95 equiv.) and 0.4 M tetrabutylammonium hydroxide (aq) (0.05 equiv.). Once the mixture returned to 0° C., epichlorohydrin (2.95 equiv.) was added portion-wise over 3 min. The mixture was stirred at room temperature for 16 hours. $H_2O$ (15 mL) was added and the mixture was extracted with EtOAc (4×30 mL). The combined extracts were washed with brine (30 mL) and dried over $Na_2SO_4$. The extracts were concentrated under reduced pressure. The residue was distilled under vacuum, providing a as a colorless liquid boiling at 110-117° C. (0.1 mmHg).

$^1$H NMR (300 MHz, $CDCl_3$, 25° C.): δ 3.85-3.40 (br m, 12H, $CH_2O(CH_2CH_2O)_2CH_2$), 3.22-3.17 (br m, 1H, $CH_b$), 2.84-2.81 (t, 1H, $CH_a$), 2.66-2.63 (m, 1H, $CH_{a'}$), 1.27-1.22 (t, 3H, $CH_3$).

Synthesis of Epoxide b:

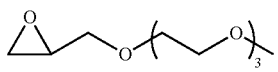

Triethylene glycol monomethyl ether (1 equiv.) and water (1 mL) were mixed together and stirred on ice before addition of NaOH (2.95 equiv.) and 0.4 M tetrabutylammonium hydroxide (aq) (0.05 equiv.). Once the mixture returned to 0° C., epichlorohydrin (2.95 equiv.) was added portion-wise over 3 min. The mixture was stirred at room temperature for 16 hours. $H_2O$ (15 mL) was added and the mixture was extracted with EtOAc (4×30 mL). The combined extracts were washed with brine (30 mL) and dried over $Na_2SO_4$. The extracts were concentrated under reduced pressure. The residue was distilled under vacuum, providing b as a colorless liquid boiling at 110-117° C. (0.1 mmHg).

$^1$H NMR (300 MHz, $CDCl_3$, 25° C.): δ 3.80-3.44 (br m, 14H, $CH_2O(CH_2CH_2O)_3$), 3.37 (s, 3H, $OCH3$), 3.15 (m, 1H, $CH_b$), 2.79 (dd, J=6.6, 5.6 Hz, 1H, $CH_a$), 2.61 (dd, J=6.7, 3.6 Hz, 1H, $CH_{a'}$).

Epoxide c:

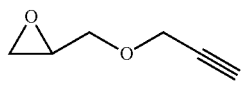

Epoxide c was purchased from Sigma Aldrich.

General Procedure for the Synthesis of 4, 5, 6, 7, and 8

A-[(VPGVG)(VPGMG)(VPGVG)$_2$]$_n$ (n=5 (SEQ ID NO: 7) or 10 (SEQ ID NO: 8)) was dissolved in glacial acetic acid (26 mg·mL$^{-1}$) under inert atmosphere ($N_2$). Epoxides a (compound 4), b (compounds 5 and 7) or c (compounds 6 and 8) was added (15 equiv. per methionine residue) and the mixture was stirred for 3 days at room temperature. The reaction mixture was transferred to 1,000 MWCO dialysis tubing and dialyzed against 0.1 M NaCl for 24 hours followed by deionized water for 48 hours with frequent water changes. The content of the dialysis bag was then lyophilized to provide alkylated ELP as a white solid.

Compound 5: $^1$H NMR (300 MHz, $D_2O$, 25° C.) (main peaks): δ 3.40 (s, 18H, $OCH_3$), 3.04-3.01 (dd, 18H, $SCH_3$), 1.00-0.75 (br m, 210H, $CH_3$ Val).

MS-ESI: Theoretical MW=10012; Experimental $(M+H)^{7+}$ m/z=1430.56

Compound 7: $^1$H NMR (300 MHz, $D_2O$, 25° C.) (main peaks): δ 3.38 (s, 33H, $OCH_3$), 3.01-2.98 (dd, 33H, $SCH_3$), 1.03-0.79 (br m, 420H, $CH_3$ Val).

Compound 8: $^1$H NMR (300 MHz, $D_2O$, 25° C.): (main peaks): δ 3.03-3.00 (dd, 33H, $SCH_3$), 1.01-0.93 (br m, 420H, $CH_3$ Val).

MS-ESI: Theoretical MW=18278, Experimental $(M)^{11+}$ m/z=1661.72

Example 4: Transition Temperature Measurements

Transition temperatures (LCSTs) were determined by measuring the turbidity at 350 nm between 20° C. and 80° C. at a 1° C.·min$^{-1}$ scan rate for ELP20, ELP20(Me) and ELP20(Bn) in PBS at three concentrations (50, 100 and 200 µM). Data were collected on a Cary 100 Bio UV-visible spectrophotometer equipped with a multi-cell thermoelectric temperature controller from Varian (Palo Alto, Calif.). The Tt is defined as the temperature corresponding to the maximum of the first derivative of the turbidity versus temperature curve.

To investigate the effect of methylation and benzylation of the ELP backbone on the LCST, turbidity assays were carried out in phosphate buffer at different concentrations.

ELP20's LCST ranged between 27° C. and 33° C. depending on the concentration (50-200 µM). After methylation, the resulting ELP20(Me) did not exhibit any LCST in the range of temperature studied. Indeed, this LCST is so high that it cannot be measured. This is most likely due to the presence of positive charges of the sulfoniums increasing the hydrophilicity of the whole polypeptide. Benzylation resulted in polypeptides that retained LCST behavior, but LCSTs were shifted to higher values indicating that the benzyl group is hydrophobic enough to partly counterbalance the hydrophilic effect of the positive charge. In order to determine whether alkylation of ELP20 also translates into changes in secondary structure, circular dichroism (CD) spectra of ELP20, ELP20(Me) and ELP20(Bn) were measured in PBS at 20° C., below all LCST values.

As usually observed with these polypeptides, ELP20 exhibited both random coil and type II β-turn secondary structure characterized by two minima at ca. 197 nm and 225 nm, respectively. Alkylation (methylation and benzylation) resulted in an overall increase of random coil structures and decrease of type II β-turns, confirming a decrease of order with increasing hydrophilicity of the ELP.

Example 5: Preparation of Other Alkylated ELP

Chemical Structure of Modified ELPs

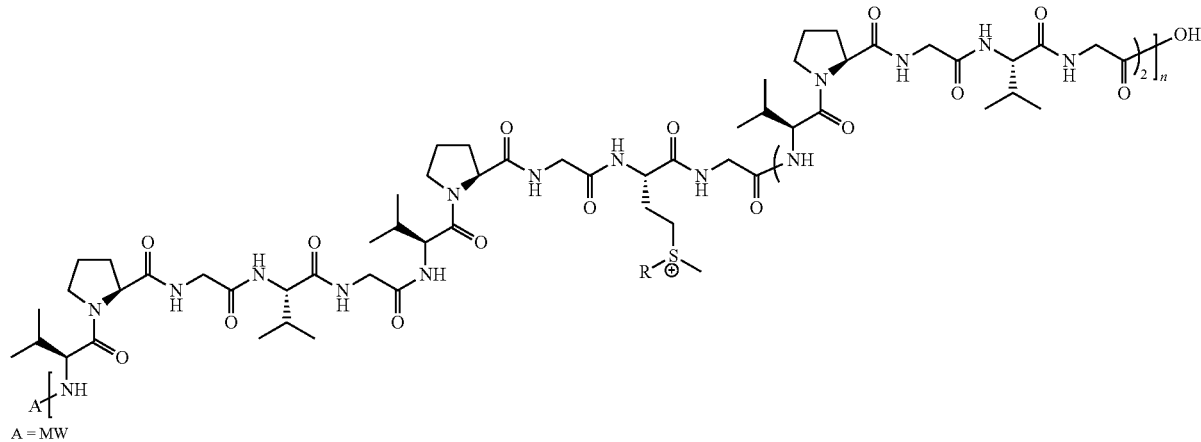

A = MW

| Chem. struct. of modif. Met | Main characteristics of product |
|---|---|
| | n = 5 (ELP-M-20) |
| | $^1$H NMR (300 MHz, D$_2$O, 25° C.): (main peaks): δ 4.5-4.4 (m, 40 H, αCH VPGXG), 4.2-4.15 (d, 15 H, αCH VPGVG), 3.04-2.9 (m, 18 H, SCH$_3$), 1.4-1.35 (d, 18 H, CHCH$_3$ Met), 1.00-0.75 (br m, 210 H, CH$_3$ Val)<br>MS-ESI: Theoretical MW = 9039.7, Experimental [M$_6$ + Na—H]$^{6+}$ = 1510.2<br>Tt (1 mM) = 35° C. |
| | $^1$H NMR (300 MHz, D$_2$O, 25° C.): (main peaks): δ 4.5-4.4 (m, 40 H, αCH VPGXG), 4.2-4.15 (d, 15 H, αCH VPGVG), 3.40 (s, 18 H, OCH$_3$ Met), 3.06-2.9 (m, 18 H, SCH$_3$), 1.00-0.75 (br m, 210 H, CH$_3$ Val)<br>MS-ESI: Theoretical MW = 10012.2, Experimental [M$_6$ + Na—H]$^{6+}$ = 1672.6<br>Tt (1 mM) = 40° C. |
| | $^1$H NMR (300 MHz, D$_2$O, 25° C.): (main peaks): δ 6-5.9 (m, 6 H, OCH$_2$CHCH$_2$ Met), 5.4-5.2 (m, 12 H, SCH$_2$CHCH$_2$), 4.5-4.4 (m, 40 H, αCH VPGXG), 4.2-4.15 (d, 15 H, αCH VPGVG), 4.15-4.05 (d, 12 H, OCH$_2$CHCH$_2$ Met), 3.06-2.9 (m, 18 H, SCH$_3$), 1.00-0.75 (br m, 210 H, CH$_3$ Val)<br>MS-ESI: Theoretical MW = 9375.9, Experimental [M$_6$]$^{6+}$ = 1562.3<br>Tt (1 mM) = 40° C. |

| Chem. struct. of modif. Met | Main characteristics of product |
|---|---|
| (structure with N, C=O, S⁺(CH₃), CH₃COO⁻, propargyl ether, OH) | ¹H NMR (300 MHz, D₂O, 25° C.): (main peaks): δ 4.5-4.4 (m, 40 H, αCH VPGXG), 4.3 (s, 12 H, OCH₂CCH Met) 4.2-4.15 (d, 15 H, αCH VPGVG), 3.06-2.9 (m, 18 H, SCH₃), 1.00-0.75 (br m, 210 H, CH₃ Val)<br>MS-ESI: Theoretical MW = 9375.9, Experimental [M₆]⁶⁺ = 1560.7<br>Tt (1 mM) = 50° C. | n = 10 (ELP-M-40)

| | |
|---|---|
| (structure with S⁺(CH₃), CH₃COO⁻, CH(OH)CH₃) | ¹H NMR (300 MHz, D₂O, 25° C.): (main peaks): δ 4.5-4.4 (m, 80 H, αCH VPGXG), 4.2-4.15 (d, 30 H, αCH VPGVG), 3.04-2.9 (m, 33 H, SCH₃), 1.4-1.35 (d, 33 H, CHCH₃ Met), 1.00-0.75 (br m, 420 H, CH₃ Val)<br>MS-ESI: Theoretical MW = 17684.9, Experimental [M₁₁]¹¹⁺ = 1607.4<br>Tt (1 mM) = 40° C. |
| (structure with S⁺(CH₃), CH₃COO⁻, PEG₃ ether, OH) | ¹H NMR (300 MHz, D₂O, 25° C.): (main peaks): δ 4.5-4.4 (m, 80 H, αCH VPGXG), 4.2-4.15 (d, 30 H, αCH VPGVG), 3.40 (s, 33 H, OCH₃ Met), 3.06-2.9 (m, 33 H, SCH₃), 1.00-0.75 (br m, 420 H, CH₃ Val)<br>MS-ESI: Theoretical MW = 19467.9, Experimental [M₁₀ + H]¹¹⁺ = 1748.9<br>Tt (1 mM) = 45° C. |
| (structure with S⁺(CH₃), CH₃COO⁻, propargyl ether, OH) | ¹H NMR (300 MHz, D₂O, 25° C.): (main peaks): δ 4.5-4.4 (m, 80 H, αCH VPGXG), 4.3 (s, 22 H, OCH₂CCH Met) 4.2-4.15 (d, 30 H, αCH VPGVG), 3.06-2.9 (m, 33 H, SCH₃), 1.00-0.75 (br m, 420 H, CH₃ Val)<br>MS-ESI: Theoretical MW = 18279.1, Experimental [M₁₁ − H]¹⁰⁺ = 1827.9<br>Tt (1 mM) = 70° C. |

Table discloses SEQ ID NOS 9, 4, 9, 4, 9, 4, 9, 4, 9, 4, 9, 4, 9, and 4, respectively, in order of appearance.

General Synthetic Procedure:

Procedure A

MW-[(VPGVG)(VPGMG)(VPGVG)₂]₅ (SEQ ID NO: 7) (ELP-M-20) was dissolved in glacial acetic acid (20 mg·mL⁻¹) and the solution was degassed by bubbling N₂ into the solution for 1 hr and then stirred under N₂. The epoxide was added (10 equiv. per methionine residue) and the mixture was stirred for 48 hrs under N₂ at room temperature. The reaction mixture was transferred to a 3,000 MWCO ultra-centrifugal filter tube and purified with 40 mL DI water. The content of the cartridge was then lyophilized to provide the modified ELP as a white solid.

Procedure B

MW-[(VPGVG)(VPGMG)(VPGVG)₂]₁₀ (SEQ ID NO: 8) (ELP-M-40) was dissolved in an AcOH/HFIP mixture (9/1, v/v) (20 mg·mL⁻¹) and the solution was degassed by bubbling N₂ into the solution for 1 hr and then stirred under N₂. The epoxide was added (10 equiv. per methionine residue) and the mixture was stirred for 48 hrs under N₂ at room temperature. The reaction mixture was transferred to a 3,000 MWCO ultra-centrifugal filter tube and purified with 40 mL DI water. The content of the cartridge was then lyophilized to provide the modified ELP as a white solid.

Example 6: Bioconjugation of Alkyne-Bearing ELPs with Azido-Functionalized Saccharides by "Click Chemistry"

This example concerns the preparation of ELPs with the below repetitive unit ("clicked" methionine residues).

Chemical Structure of Alkyne-Bearing Methionine Residues:

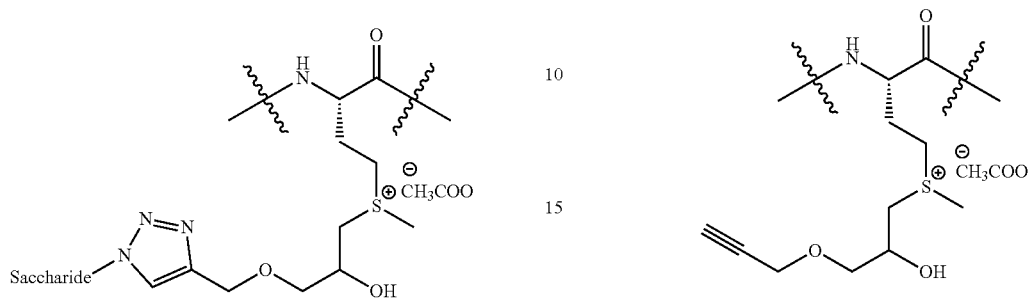

| Chem. struct. of the azido-saccharide | Main characteristics of product |
|---|---|
| n = 5 (ELP-M-20) | |
| (mannose-N₃ structure) | ¹H NMR (300 MHz, D₂O, 25° C.): (main peaks): δ 8.4-8.3 (br s, 6 H, triazole-H) 5.9-5.8 (br s, 6 H, anomeric-H), 4.22-4.16 (m, 40 H, αCH VPGXG), 4.2-4.15 (d, 15 H, αCH VPGVG), 3.06-2.9 (m, 18 H, SCH₃), 1.00-0.75 (br m, 210 H, CH₃ Val) Tt (1 mM) = 45° C. |
| (saccharide-N₃ structure) | ¹H NMR (300 MHz, D₂O, 25° C.): (main peaks): δ 8.35-8.3 (br s, 6 H, triazole-H) 5.7-5.65 (br s, 6 H, anomeric-H), 4.5-4.4 (m, 40 H, αCH VPGXG), 4.22-4.16 (d, 15 H, αCH VPGVG), 3.06-2.9 (m, 18H, SCH₃), 1.00-0.75 (br m, 210 H, CH₃ Val) Tt (1 mM) = 40° C. |
| (saccharide-N₃ structure) | ¹H NMR (300 MHz, D₂O, 25° C.): (main peaks): δ 8.29-8.25 (br s, 6 H, triazole-H) 6.2-6.1 (br s, 6 H, anomeric-H), 4.22-4.16 (m, 40 H, αCH VPGXG), 4.2-4.15 (d, 15 H, αCH VPGVG), 3.06-2.9 (m, 18 H, SCH₃), 1.00-0.75 (br m, 210 H, CH₃ Val) Tt (1 mM) = 35° C. |
| n = 10 (ELP-M-40) | |
| (saccharide-N₃ structure) | ¹H NMR (300 MHz, D₂O, 25° C.): (main peaks): δ 8.4-8.3 (br s, 11 H, triazole-H) 5.9-5.75 (br s, 11 H, anomeric-H), 4.5-4.4 (m, 80 H, αCH VPGXG), 4.2-4.15 (d, 30 H, αCH VPGVG), 3.06-2.9 (m, 33 H, SCH₃), 1.00-0.75 (br m, 420 H, CH₃ Val) Tt (1 mM) = 65° C. |
| (saccharide-N₃ structure) | ¹H NMR (300 MHz, D₂O, 25° C.): (main peaks): δ 8.4-8.3 (br s, 11 H, triazole-H) 5.85-5.7 (br s, 11 H, anomeric-H), 4.5-4.4 (m, 80 H, αCH VPGXG), 4.2-4.15 (d, 30 H, αCH VPGVG), 3.06-2.9 (m, 33 H, SCH₃), 1.00-0.75 (br m, 420 H, CH₃ Val) Tt (1 mM) = 40° C. |

| Chem. struct. of the azido-saccharide | Main characteristics of product |
|---|---|
| (α-D-mannopyranosyl azide structure: OH, OH, HO, HO, N₃) | ¹H NMR (300 MHz, D₂O, 25° C.): (main peaks): δ 8.25-8.22 (br s, 11 H, triazole-H) 6.16-6.12 (br s, 11 H, anomeric-H), 4.5-4.4 (m, 80 H, αCH VPGXG), 4.2-4.15 (d, 30 H, αCH VPGVG), 3.06-2.9 (m, 33 H, SCH₃), 1.00-0.75 (br m, 420 H, CH₃ Val) Tt (1 mM) = 40° C. |

Table discloses SEQ ID NOS 9, 4, 9, 4, 9, 4, 9, 4, 9, 4, 9, and 4, respectively, in order of appearance.

General Synthetic Procedure:

Procedure A

The alkyne bearing ELP-M-n was dissolved in water (5 mg/mL) and the desired azido sugar (1.5 equiv./alkyne) was added. The solution was degassed by bubbling $N_2$ into the solution for 2 hrs and then stirred under $N_2$. Separately, a solution of Cu(I) was prepared by addition of sodium ascorbate (0.65 equiv./alkyne) to a degassed solution of Cu(II)SO₄ (0.13 equiv./alkyne) and pentamethyldiethylenetriamine (0.13 equiv./alkyne). The Cu(I) solution was transferred to the reaction mixture via syringe. The reaction was stirred at room temperature for 72 hrs. The solution was transferred to a 3,000 MWCO ultra-centrifugal filter tube and purified with an EDTA solution and then with 40 mL DI water. The content of the cartridge was then lyophilized to provide the glycosylated ELP as a white solid.

Procedure B

The alkyne bearing ELP-M-40 was dissolved in previously vacuum degassed water (5 mg/mL), α-D-mannopyranosyl azide (1.5 equiv./alkyne) was added and the mixture was stirred under $N_2$. Separately, a solution of Cu(I) was prepared by addition of sodium ascorbate (0.65 equiv./alkyne) to a degassed solution of Cu(II)SO₄ (0.13 equiv./alkyne) and pentamethyldiethylenetriamine (0.13 equiv./alkyne). The solution turned dark blue. The Cu(I) solution was transferred to the reaction mixture with a syringe. The reaction was stirred at room temperature for 72 hrs. The solution was transferred to a 3,000 MWCO ultra-centrifugal filter tube and purified with an EDTA solution and then with 40 mL DI water. The content of the cartridge was then lyophilized to provide the glycosylated ELP as a white solid.

Example 7: Counter-Ion Exchange and Tuning of the Transition Temperature (Tt)

Chemical Structure of ELP:

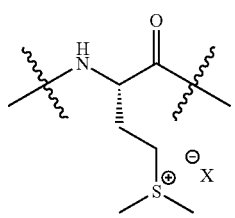

| Nature of counterion (X⁻) | Main characteristics of product |
|---|---|
| I⁻ | Tt (2 mM) = 70° C. |
| CH₃COO⁻ | Tt (2 mM) = 50° C. |
| CF₃COO⁻ | Tt (2 mM) = 40° C. |
| PF₆⁻ | Tt (2 mM) = 50° C. |
| NTf₂⁻ | Tt (2 mM) = 31° C. |
| (H₃CO, CF₃, phenyl, carboxylate — one enantiomer) | Tt (2 mM) = 40° C. |
| (H₃CO, CF₃, phenyl, carboxylate — other enantiomer) | Tt (2 mM) = 34° C. |

General Synthetic Procedure for Ion Exchange:

MW-[(VPGVG)(VPGMG)(VPGVG)₂]₁₀ (SEQ ID NO: 8) (ELP-M-40) was dissolved in 0.2 M aqueous formic acid (20 mg/mL). Iodomethane (15 equiv. per Met residue) was added as a solution in THF (50 mg/mL). The reaction was sealed, covered with foil, and stirred for 4 days at room temperature. Diethyl ether (equal to about half the reaction volume) was added to the reaction to extract the excess alkyl halide. The biphasic reaction was vortexed briefly and then allowed to sit until separation of the phases. The ether layer was pipetted off and discarded. The reaction mixture was transferred to a 3,000 MWCO ultra-centrifugal filter tube and purified with 40 mL DI water. The content of the cartridge was then lyophilized to provide the modified ELP as a white solid.

The methylated ELP-M-40 previously synthesized was suspended in water and added dropwise to a solution of the desired salt (NaX or LiX, 5 equiv. per sulfonium). The mixture was stirred overnight at room temperature or at 10° C. for the most hydrophobic counterions. The solution was transferred to a 3,000 MWCO ultra-centrifugal filter tube and purified a couple times with DI water to remove the excess salt. The content of the cartridge was then added dropwise to a new solution of salt (5 equiv. per sulfonium) and stirred overnight. The solution was purified with 40 mL DI water using a 3,000 MWCO ultra-centrifugal filter tube. The content of the cartridge was then lyophilized to provide the modified ELP as a white solid.

The invention claimed is:

1. A process for modulating the lower critical solution temperature of an elastin-like polypeptide comprising at least one methionine residue, said process comprising a thioether alkylation step of said elastin-like polypeptide.

2. A compound comprising at least one repetitive unit having the following formula (I):

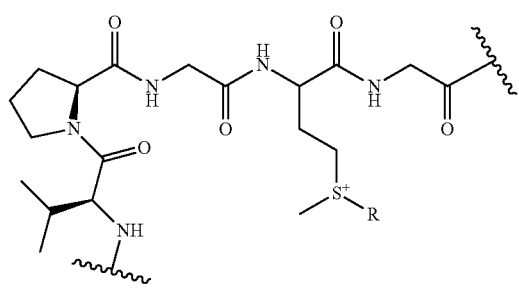

(I)

wherein R is selected from the group consisting of:
($C_1$-$C_{22}$)alkyl groups;
said alkyl groups being possibly substituted by one or several substituents selected from the group consisting of: OH, $OR_a$, $NR_bR_c$, and $NHC(O)R_c$,
$R_a$ being selected from the group consisting of: ($C_1$-$C_{10}$) alkyl groups possibly interrupted by one or several heteroatom(s), ($C_1$-$C_{10}$)alkylene-($C_2$-$C_{10}$)alkyne groups, ($C_1$-$C_{10}$)alkylene-($C_2$-$C_{10}$)alkenyl groups, and ($C_1$-$C_{10}$)alkylene-X' groups;
X' representing a radical having the following formula:

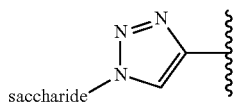

$R_b$ and $R_c$ representing independently from each other H or a ($C_1$-$C_{10}$)alkyl group;
($C_1$-$C_{22}$)alkylene-($C_6$-$C_{30}$)aryl groups;
($C_6$-$C_{30}$)aryl groups;
($C_2$-$C_{22}$)alkyne groups; and
saccharides.

3. The compound of claim 2, having the following formula (II):

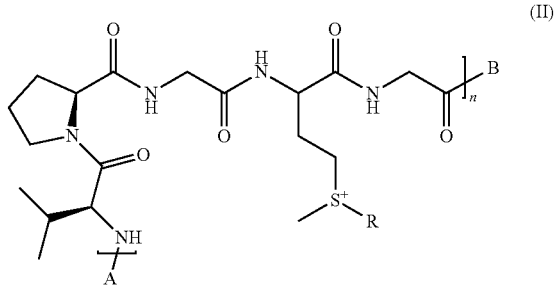

(II)

wherein:
n is an integer varying from 1 to 200, and
A is selected from the group consisting of: H, acetyl, natural or unnatural amino acids, peptides, proteins and synthetic polymers; and
B is selected from the group consisting of: OH, $NH_2$, NHAc, natural or unnatural amino acids, peptides, proteins, and synthetic polymers.

4. The compound of claim 3, wherein A is selected from the group consisting of peptides and natural or unnatural amino acids.

5. The compound of claim 3, wherein B is OH or is selected from the group consisting of peptides and natural or unnatural amino acids.

6. The compound of claim 2, having the following formula (III):

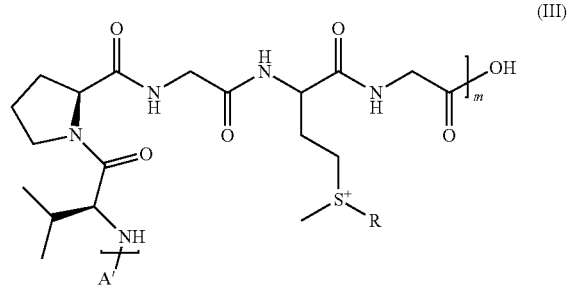

(III)

wherein:
m is an integer varying from 1 to 200, and
A' is a peptide comprising from 1 to 20 amino acids.

7. The compound of claim 2, having the following formula (IV):

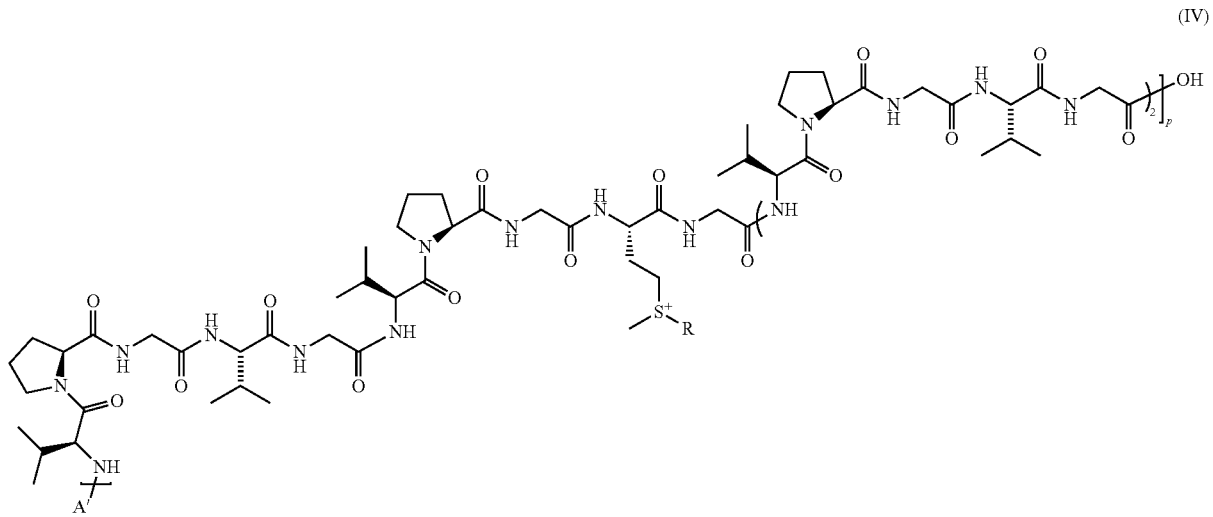

wherein:
p is an integer varying from 1 to 200, and
A" is a peptide comprising from 1 to 20 amino acids.

8. The compound of claim 2, wherein R is selected from the group consisting of:
($C_1$-$C_{22}$)alkyl groups; and
($C_1$-$C_{22}$)alkylene-phenyl groups.

9. The compound of claim 2, wherein R is -$A_1$-CH(OH)-$A_2$-O-$A_3$-$A_4$, wherein:
$A_1$ is a ($C_1$-$C_4$)alkylene radical;
$A_2$ is a ($C_1$-$C_4$) alkylene radical;
$A_3$ is a ($C_1$-$C_4$)alkylene radical or a —($CH_2$—$CH_2$—O)$_i$— group, i being an integer varying from 1 to 4, and
$A_4$ is a ($C_1$-$C_4$)alkylene radical or a ($C_2$-$C_4$)alkyne group.

10. The compound of claim 2, wherein R is a ($C_1$-$C_4$)alkyl or benzyl group.

11. A thioether alkylation process for preparing a compound according to claim 2, comprising a thioether alkylation step of an elastin-like polypeptide comprising at least one repetitive unit having the following formula (V):

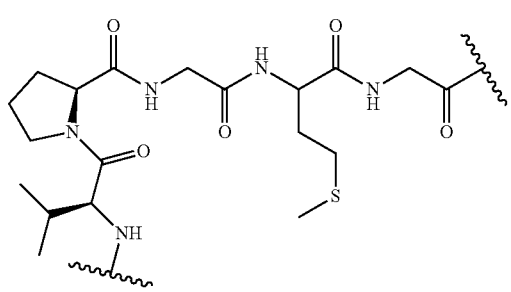

said thioether alkylation step consisting in the reaction with an alkylation agent.

12. The thioether alkylation process of claim 11, wherein the alkylation agent is a compound of formula (III) R—X, and X being a halogen atom, or a compound of formula (III-1):

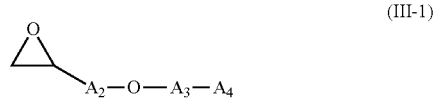

wherein:
$A_2$ is a ($C_1$-$C_4$)alkylene radical;
$A_3$ is a ($C_1$-$C_4$)alkylene radical or a —($CH_2$—$CH_2$—O)$_i$— group, i being an integer varying from 1 to 4, and
$A_4$ is a ($C_1$-$C_4$)alkylene radical or a ($C_2$-$C_4$)alkyne group.

13. A process for modulating the lower critical solution temperature of an elastin-like polypeptide, said process comprising a thioether alkylation step of an elastin-like polypeptide comprising at least one repetitive unit having the following formula (V):

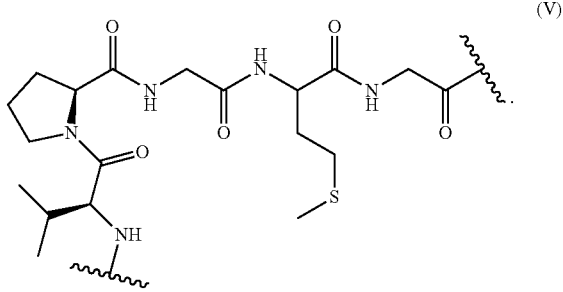 [SMILES: *N[C@H](C(=O)N1CCC[C@H]1C(=O)NCC(=O)NC(CCSC)C(=O)NCC(*)=O)C(C)C]

14. The process for modulating the lower critical solution temperature of claim 13, wherein the thioether alkylation step consists in reacting the elastin-like polypeptide with a compound of formula (III) R—X, and X being a halogen atom, and R being selected from the group consisting of:
($C_1$-$C_{22}$)alkyl groups;
said alkyl groups being possibly substituted by one or several substituents selected from the group consisting of: OH, O$R_a$, N$R_b$$R_c$, and NHC(O)$R_c$,
$R_a$ being selected from the group consisting of: ($C_1$-$C_{10}$)alkyl groups possibly interrupted by one or several heteroatom(s), ($C_1$-$C_{10}$)alkylene-($C_2$-$C_{10}$) alkyne groups, ($C_1$-$C_{10}$)alkylene-($C_2$-$C_{10}$)alkenyl groups, and ($C_1$-$C_{10}$)alkylene-X' groups;

X' representing a radical having the following formula:

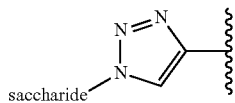

$R_b$ and $R_c$ representing independently from each other H or a $(C_1-C_{10})$alkyl group;
$(C_1-C_{22})$alkylene-$(C_6-C_{30})$aryl groups;
$(C_6-C_{30})$aryl groups;
$(C_2-C_{22})$alkyne groups; and
saccharides.

15. A compound comprising at least one repetitive unit having the following formula (I'):

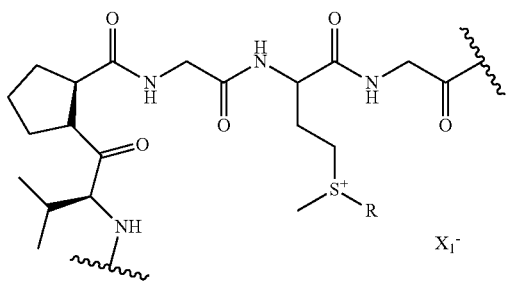

wherein:
$X_1$ is a counterion,
R is selected from the group consisting of:
$(C_1-C_{22})$alkyl groups;
said alkyl groups being possibly substituted by one or several substituents selected from the group consisting of: OH, $OR_a$, $NR_bR_c$, and $NHC(O)R_c$,
$R_a$ being selected from the group consisting of: $(C_1-C_{10})$ alkyl groups possibly interrupted by one or several heteroatom(s), $(C_1-C_{10})$alkylene-$(C_2-C_{10})$alkyne groups, $(C_1-C_{10})$alkylene-$(C_2-C_{10})$alkenyl groups, and $(C_1-C_{10})$alkylene-X' groups;
X' representing a radical having the following formula:

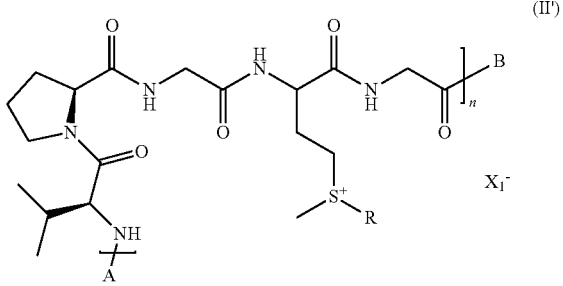

$R_b$ and $R_c$ representing independently from each other H or a $(C_1-C_{10})$alkyl group;
$(C_1-C_{22})$alkylene-$(C_6-C_{30})$aryl groups;
$(C_6-C_{30})$aryl groups;
$(C_2-C_{22})$alkyne groups; and
saccharides.

16. The compound of claim 15, having the following formula (II'):

wherein:
$X_1$ is a counterion,
n is an integer varying from 1 to 200, and
A is selected from the group consisting of: H, acetyl, natural or unnatural amino acids, peptides, proteins and synthetic polymers; and
B is selected from the group consisting of: OH, $NH_2$, NHAc, natural or unnatural amino acids, peptides, proteins, and synthetic polymers.

* * * * *

SEQUENCE LISTING

<160> NUMBER OF SEQ ID NOS: 9

<210> SEQ ID NO 1
<211> LENGTH: 365
<212> TYPE: DNA
<213> ORGANISM: Artificial Sequence
<220> FEATURE:
<223> OTHER INFORMATION: Description of Artificial Sequence: Synthetic
      ELP polynucleotide
<220> FEATURE:
<221> NAME/KEY: CDS
<222> LOCATION: (4)..(348)
<220> FEATURE:
<221> NAME/KEY: misc_feature
<222> LOCATION: (4)..(48)
<223> OTHER INFORMATION: Leader sequence

<400> SEQUENCE: 1

```
cat atg ggt acc gag ctc gcg gcc gca agc gaa ttc aca cat atg tgg      48
    Met Gly Thr Glu Leu Ala Ala Ala Ser Glu Phe Thr His Met Trp
    1               5                   10                  15 gta ccg gga atg ggt gtg ccc ggc atg ggc gta cct ggt atg gga gtc      96
Val Pro Gly Met Gly Val Pro Gly Met Gly Val Pro Gly Met Gly Val
                20                  25                  30 ccg ggg atg ggc gtt cca ggg atg gga gtc cca ggg atg ggt gta ccg     144
Pro Gly Met Gly Val Pro Gly Met Gly Val Pro Gly Met Gly Val Pro
            35                  40                  45 ggc atg gga gtg ccg gga atg ggc gta ccg ggg atg ggt gtg cct ggt     192
Gly Met Gly Val Pro Gly Met Gly Val Pro Gly Met Gly Val Pro Gly
        50                  55                  60 atg ggt gtc ccc ggt atg gga gtt ccc ggc atg ggc gtt cca ggc atg     240
Met Gly Val Pro Gly Met Gly Val Pro Gly Met Gly Val Pro Gly Met
65                  70                  75                  80 ggt gtg ccg ggt atg gga gta ccg ggt atg ggt gta cca gga atg ggc     288
Gly Val Pro Gly Met Gly Val Pro Gly Met Gly Val Pro Gly Met Gly
                85                  90                  95 gtg cct ggc atg gga gta cca ggc atg ggc gtc ccc ggg atg ggt gtt     336
Val Pro Gly Met Gly Val Pro Gly Met Gly Val Pro Gly Met Gly Val
            100                 105                 110 ccc ggt atg ggg taaaggatcc aaagctt                                   365
Pro Gly Met Gly
        115
```

<210> SEQ ID NO 2
<211> LENGTH: 115
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

```
Met Gly Thr Glu Leu Ala Ala Ala Ser Glu Phe Thr His Met Trp Val
1               5                   10                  15

Pro Gly Met Gly Val Pro Gly Met Gly Val Pro Gly Met Gly Val Pro
            20                  25                  30

Gly Met Gly Val Pro Gly Met Gly Val Pro Gly Met Gly Val Pro Gly
        35                  40                  45

Met Gly Val Pro Gly Met Gly Val Pro Gly Met Gly Val Pro Gly Met
    50                  55                  60

Gly Val Pro Gly Met Gly Val Pro Gly Met Gly Val Pro Gly Met Gly
65                  70                  75                  80

Val Pro Gly Met Gly Val Pro Gly Met Gly Val Pro Gly Met Gly Val
```

```
                    85                  90                  95
Pro Gly Met Gly Val Pro Gly Met Gly Val Pro Gly Met Gly Val Pro
                100                 105                 110
Gly Met Gly
        115

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      pentapeptide
<220> FEATURE:
<221> NAME/KEY: MOD_RES
<222> LOCATION: (4)..(4)
<223> OTHER INFORMATION: Any amino acid except Pro

<400> SEQUENCE: 3

Val Pro Gly Xaa Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Pro Gly Val Gly
1               5

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Gly Thr Glu Leu Ala Ala Ala Ser Glu Phe Thr His Met Trp
1               5                   10                  15

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Pro Gly Met Gly
1               5

<210> SEQ ID NO 7
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

Met Trp Val Pro Gly Val Gly Val Pro Gly Met Gly Val Pro Gly Val
1               5                   10                  15

Gly Val Pro Gly Val Gly Val Pro Gly Val Gly Val Pro Gly Met Gly
                20                  25                  30

Val Pro Gly Val Gly Val Pro Gly Val Gly Val Pro Gly Val Gly Val
            35                  40                  45

Pro Gly Met Gly Val Pro Gly Val Gly Val Pro Gly Val Gly Val Pro
        50                  55                  60

Gly Val Gly Val Pro Gly Met Gly Val Pro Gly Val Gly Val Pro Gly
65                  70                  75                  80

Val Gly Val Pro Gly Val Gly Val Pro Gly Met Gly Val Pro Gly Val
                85                  90                  95

Gly Val Pro Gly Val Gly
            100

<210> SEQ ID NO 8
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Trp Val Pro Gly Val Gly Val Pro Gly Met Gly Val Pro Gly Val
1               5                   10                  15

Gly Val Pro Gly Val Gly Val Pro Gly Val Gly Val Pro Gly Met Gly
                20                  25                  30

Val Pro Gly Val Gly Val Pro Gly Val Gly Val Pro Gly Val Gly Val
            35                  40                  45

Pro Gly Met Gly Val Pro Gly Val Gly Val Pro Gly Val Gly Val Pro
        50                  55                  60

Gly Val Gly Val Pro Gly Met Gly Val Pro Gly Val Gly Val Pro Gly
65                  70                  75                  80

Val Gly Val Pro Gly Val Gly Val Pro Gly Met Gly Val Pro Gly Val
                85                  90                  95

Gly Val Pro Gly Val Gly Val Pro Gly Val Gly Val Pro Gly Met Gly
            100                 105                 110

Val Pro Gly Val Gly Val Pro Gly Val Gly Val Pro Gly Val Gly Val
        115                 120                 125

Pro Gly Met Gly Val Pro Gly Val Gly Val Pro Gly Val Gly Val Pro
    130                 135                 140

Gly Val Gly Val Pro Gly Met Gly Val Pro Gly Val Gly Val Pro Gly
145                 150                 155                 160

Val Gly Val Pro Gly Val Gly Val Pro Gly Met Gly Val Pro Gly Val
                165                 170                 175

Gly Val Pro Gly Val Gly Val Pro Gly Val Gly Val Pro Gly Met Gly
            180                 185                 190

Val Pro Gly Val Gly Val Pro Gly Val Gly
        195                 200

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (4)..(4)
<223> OTHER INFORMATION: Any amino acid

<400> SEQUENCE: 9

Val Pro Gly Xaa Gly
1               5
```